US00PP13282P2

(12) United States Plant Patent
Heims

(10) Patent No.: US PP13,282 P2
(45) Date of Patent: Nov. 26, 2002

(54) CAMPANULA PLANT NAMED 'PANTALOONS'

(75) Inventor: Daniel M. Heims, Portland, OR (US)

(73) Assignee: Terra Nova Nurseries, Inc., Tigard, OR (US)

( * ) Notice: Subject to any disclaimer, the term of this patent is extended or adjusted under 35 U.S.C. 154(b) by 0 days.

(21) Appl. No.: 09/990,008

(22) Filed: Nov. 20, 2001

(51) Int. Cl.[7] ..... A01H 5/00
(52) U.S. Cl. ..... Plt./263
(58) Field of Search ..... Plt./263

*Primary Examiner*—Bruce Campell
*Assistant Examiner*—A H Para
(74) *Attorney, Agent, or Firm*—Klarquist Sparkman, LLP

(57) ABSTRACT

A new and distinct hybrid of Campanula plant characterized by semi-double, light purple flowers.

1 Drawing Sheet

BOTANICAL CLASSIFICATION

*Campanula punctata.*

VARIETY DENOMINATION

'Pantaloons'.

ORIGIN OF THE PLANT

The present invention relates to a new and distinct hybrid of *Campanula punctata*, of the family Campanulaceae, which originated from an open-pollination of *Campanula punctata* 'Wedding Bells', an unpatented plant (seed parent). It is unknown whether this is the result of a self-pollination or an outcross.

The new variety has been reproduced only by asexual propagation (division and tissue culture). Each of the progeny exhibits identical characteristics to the original plant.

SUMMARY OF THE INVENTION

This plant is characterized by the following:

1. Unusual flower type as it is a semi-double with the outside corolla covering the top one to two thirds of the inside corolla and reflexing back, looking like a skirt.
2. Numerous large, light purple flowers held above the foliage.

Asexual propagation by tissue culture using standard micropropagation techniques with terminal and lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The FIGURE shows a young Campanula 'Pantaloons' in flower in a test garden in Canby, Oreg.

DETAILED PLANT DESCRIPTION

The following is a detailed description of the new Campanula hybrid based on observations of a one-and-a-half year old specimen grown in a one-gallon pot in a cool greenhouse in Canby, Oreg. The color descriptions are all based on The Royal Horticultural Society Colour Chart.

Botanical classification: *Campanula punctata.*
Market class: Herbaceous perennial.
Plant:
- *Type.*—Herbaceous perennial.
- *Hardiness.*—USDA Zones 4 to 9.
- *Size.*—30 cm. wide and 20 cm. tall. (In the garden the plant will grow to 60 cm tall).
- *Form.*—Basal clump.

Leaf:
- *Type.*—Simple.
- *Shape.*—Ovate-cordate.
- *Arrangement.*—Rosette.
- *Blade length.*—8 cm.
- *Blade width.*—6 cm. at the widest part.
- *Margins.*—Doubly serrate.
- *Apex.*—Acute.
- *Base.*—Cordate.
- *Venation.*—Pinnate.
- *Texture.*—Hispid.
- *Petiole length.*—14 cm., clasping at the base.
- *Petiole texture.*—Hispid.
- *Petiole color.*—Between Yellow Green152A and 147A except where in the sun, then it is Grey Brown 199A to Grey Purple 187B.
- *Leaf color.*—Topside — Grass green, between Green 138A and Yellow Green 144A. In bright light leaf gets maroon colored on veins, Greyed Purple 187A Bottom-side — Closest to Green 138B.

Inflorescence:
- *Type.*—Terminal panicle.
- *Peduncle.*—Height: 62 cm. Diameter: 0.4 cm. at widest. Texture: Hispid. Color: Yellow Green 144A, with an overlay of maroon, Greyed Purple 183A.
- *Pedicel.*—Length: 0.5 to 2.3 cm. Texture: Hispid. Color: Yellow Green 144A.
- *Flower number.*—Approximately 17 per panicle.

Flower bud:
- *Size.*—3.5 cm. deep and 3 cm. wide at the skirt where it is the widest.
- *Shape.*—Ovoid inner corolla, campanulate outer corolla.
- *Color.*—Dull grey purple, closest to Purple 77A but duller.

*Texture.*—Smooth.
*Aspect.*—Shiny.

Flower:
*Type.*—Actinomorphic, semi-double.
*Shape.*—Campanulate, inner corolla normal, outer corolla less than ½ the size.
*Size.*—Inner corolla: 5 cm. deep and 3.8 cm. wide at the lobes where they reflex slightly. Outer corolla: 2.5 cm deep and 5 cm wide at the skirt or lobes, which reflex and curl sharply.
*Lobes.*—Inner corolla: 1.3 cm deep and 1.5 cm wide at base. Outer corolla: 1.5 cm deep and 1.5 cm wide at base. Curl back sharply.
*Texture.*—Villous inside corollas.
*Color.*—Outside is closest to Violet 84B but duller. Inside is White 155D spotted with Red Purple 72A on veins and near base and Purple 76B where lighter.
*Calyx.*—None.
*Pistil.*—2.3 cm. long, White 155A, stigma 3-parted.
*Stamen number.*—5.
*Filament length.*—0.3 cm.
*Anther size before dehiscing.*—1 cm.
*Pollen color.*—Cream, Greyed Yellow 158B.
*Bloom period.*—May through July in Canby, Oreg. It will rebloom when cut back if climates are mild.
*Fragrance.*—None.

Fruit:
*Type.*—3-celled capsule.
*Color.*—Tan, Grey Brown 199D.

Seed:
*Color.*—Grey Brown 199A.
*Size.*—About 1 mm. long.
*Shape.*—Oval.
*Fertility.*—Fertile.

Disease: None observed on plant grown under commercial conditions in Canby, Oreg.

COMPARISONS TO SIMILAR CAMPANULA

Compared to *Campanula punctata* 'Cherry Bells', an unpatented plant, this new cultivated variety is a semi-double with lighter light purple flowers rather than rose pink.

Compared to *Campanula punctata* 'Wedding Bells', an unpatented plant, this new variety is semi-double rather than double and light purple rather than white, blushed pink.

I claim:

1. A new and distinct hybrid of Campanula plant substantially as shown and described, characterized by a semi-double, light purple flowers.

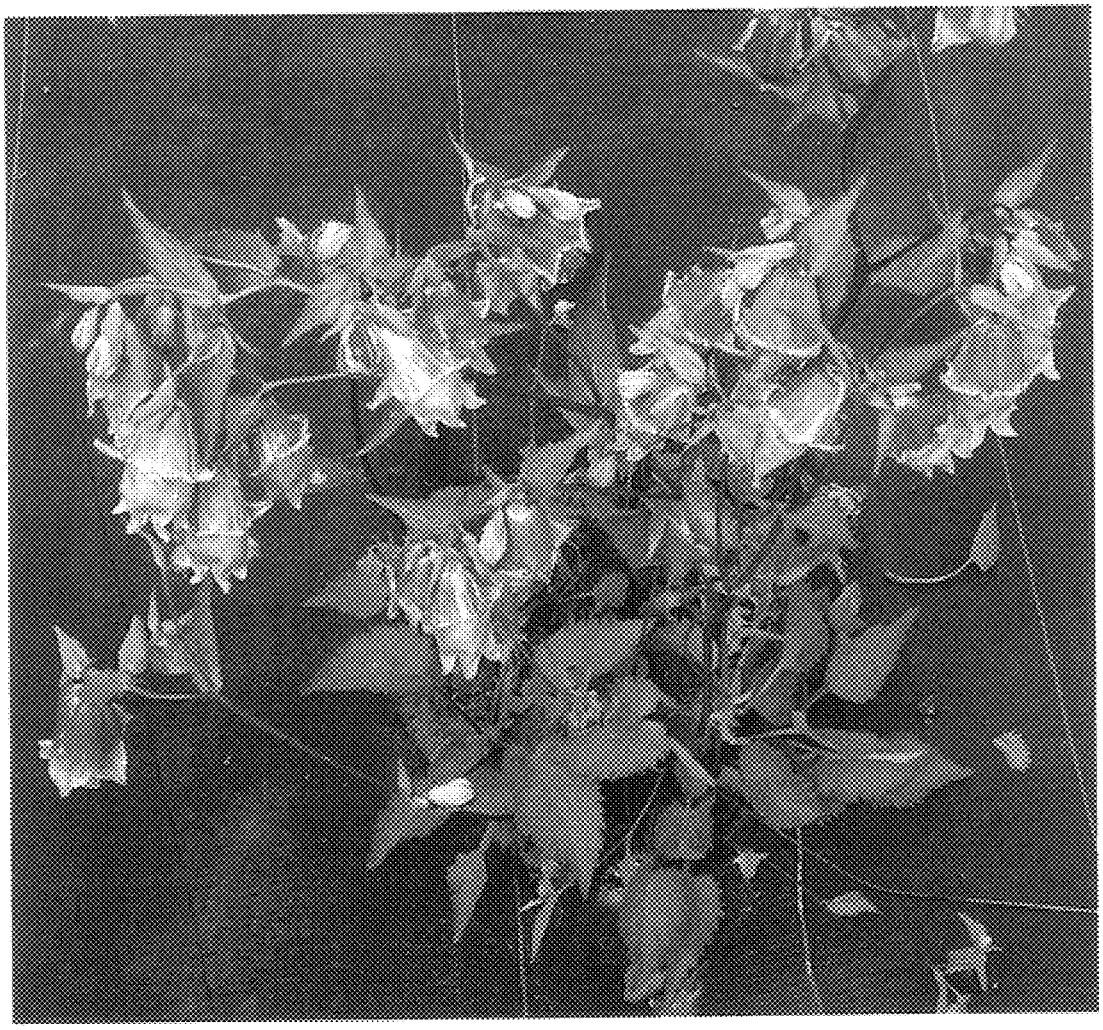

* * * * *